United States Patent
Hamauzu (10) Patent No.: US 12,026,927 B2
(45) Date of Patent: Jul. 2, 2024

(54) LEARNING DEVICE, LEARNING METHOD, LEARNING PROGRAM, TRAINED MODEL, RADIOGRAPHIC IMAGE PROCESSING DEVICE, RADIOGRAPHIC IMAGE PROCESSING METHOD, AND RADIOGRAPHIC IMAGE PROCESSING PROGRAM

(71) Applicant: FUJIFILM Corporation, Tokyo (JP)

(72) Inventor: Shin Hamauzu, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 414 days.

(21) Appl. No.: 17/469,472

(22) Filed: Sep. 8, 2021

(65) Prior Publication Data
US 2022/0083805 A1    Mar. 17, 2022

(30) Foreign Application Priority Data
Sep. 15, 2020   (JP) ................. 2020-154639

(51) Int. Cl.
*G06V 10/00* (2022.01)
*G06F 18/214* (2023.01)
(Continued)

(52) U.S. Cl.
CPC ............ *G06V 10/25* (2022.01); *G06F 18/214* (2023.01); *G06T 7/0012* (2013.01); *G06V 20/00* (2022.01);
(Continued)

(58) Field of Classification Search
CPC ............ G06N 3/08; G06N 20/00; G06N 3/02; G06K 9/3233; G06K 9/00624; G06K 9/6256; G06K 9/2054; G06K 2209/057; G06T 7/0012; G06T 7/73; G06T 7/11; G06T 2207/20081; G06T 2207/20084;
(Continued)

(56) References Cited

U.S. PATENT DOCUMENTS 7,048,682 B2 *   5/2006   Neisz ................. A61B 17/0401
                                                              600/30
7,837,613 B2 *  11/2010   Lashinski ........ A61B 17/06066
                                                              623/8
(Continued)

FOREIGN PATENT DOCUMENTS

JP   2010-131371 A   6/2010
JP   2015-058112 A   3/2015
(Continued)

OTHER PUBLICATIONS

Nathaniel, Ram, "DE202013100353U1 Devices, systems, circuits and associated computer-executable code for detecting and predicting the position, orientation and trajectory of surgical tools"; Publication Date: May 3, 2013.*

(Continued)

*Primary Examiner* — Amir Alavi
(74) *Attorney, Agent, or Firm* — Studebaker & Brackett PC (57) ABSTRACT

A processor performs machine learning, which uses a radiographic image that does not include a suture needle as a surgical tool and a surgical tool image that includes the suture needle in a posture different from a linear posture as training data, to construct a trained model for detecting a region of the suture needle from an input radiographic image.

11 Claims, 8 Drawing Sheets

(51) Int. Cl.
  *G06T 7/00* (2017.01)
  *G06V 10/25* (2022.01)
  *G06V 20/00* (2022.01)
  *G16H 50/20* (2018.01)

(52) U.S. Cl.
  CPC .... *G16H 50/20* (2018.01); *G06T 2207/10116* (2013.01); *G06T 2207/20081* (2013.01); *G06T 2207/20221* (2013.01); *G06T 2207/30004* (2013.01); *G06V 2201/034* (2022.01)

(58) Field of Classification Search
  CPC ........... G06T 2207/30004; G06T 2207/20221; G06T 2207/10116; G06T 2207/30052; A61B 6/463; A61B 6/12; A61B 17/3211; A61B 17/3201; A61B 17/06066; A61B 17/29; G16H 50/20; G16H 30/40; G06V 2201/034; G06V 20/00; G06F 18/24; A61F 13/44; A61F 2/07
  See application file for complete search history.

(56) References Cited

U.S. PATENT DOCUMENTS

| | | | |
|---|---|---|---|
| 8,029,482 B2* | 10/2011 | Maniar | A61M 39/0247 604/288.02 |
| 9,317,920 B2* | 4/2016 | Gluncic | A61B 8/5215 |
| 9,579,090 B1* | 2/2017 | Simms | A61B 17/00234 |
| 9,947,090 B2* | 4/2018 | Agam | G06V 10/774 |
| 11,389,248 B1* | 7/2022 | Roh | G05B 13/0265 |
| 11,464,590 B1* | 10/2022 | Roh | A61B 34/37 |
| 11,504,192 B2* | 11/2022 | Shelton, IV | G16H 40/63 |
| 2013/0136323 A1 | 5/2013 | Asiyanbola et al. | |
| 2014/0051991 A1 | 2/2014 | Sakaguchi et al. | |
| 2016/0071264 A1* | 3/2016 | Agam | G06V 10/774 382/128 |
| 2021/0063323 A1 | 3/2021 | Nakatani et al. | |
| 2021/0251583 A1* | 8/2021 | Hamauzu | A61B 17/3201 |
| 2022/0083805 A1* | 3/2022 | Hamauzu | G06T 7/0012 |

FOREIGN PATENT DOCUMENTS

| | | |
|---|---|---|
| JP | 2017-185007 A | 10/2017 |
| JP | 2018-068863 A | 5/2018 |
| WO | 2019/159440 A1 | 8/2019 |

OTHER PUBLICATIONS

An Office Action mailed by the Japanese Patent Office on Jul. 4, 2023, which corresponds to Japanese Patent Application No. 2020-154639 and is related to U.S. Appl. No. 17/469,472; with English language translation.

* cited by examiner

LEARNING DEVICE, LEARNING METHOD, LEARNING PROGRAM, TRAINED MODEL, RADIOGRAPHIC IMAGE PROCESSING DEVICE, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2020-154639 filed on Sep. 15, 2020. The above application is hereby expressly incorporated by reference, in its entirety, into the present application.

BACKGROUND

Technical Field

The present disclosure relates to a learning device, a learning method, a learning program, a trained model, a radiographic image processing device, a radiographic image processing method, and a radiographic image processing program.

Related Art

Various surgical tools, such as gauze to suppress bleeding, a thread and a suture needle for sewing up a wound or an incision, a scalpel and scissors for incision, a drain for draining blood, and forceps for opening an incision, are used in a case in which a surgical operation is performed for a patient. The surgical tools may cause serious complications in a case in which they remain in the body of the patient after surgery.

Therefore, a method has been proposed which prepares a discriminator as a trained model that has learned the characteristics of a gauze image and inputs an image acquired by capturing a surgical field with a camera to a discriminator to discriminate whether or not gauze is present (see JP2018-068863A).

SUMMARY OF THE INVENTION

However, since gauze is stained with blood, it is difficult to find gauze in the image acquired by the camera even in a case in which the discriminator is used. Further, a small surgical tool, such as a suture needle, is likely to go between the internal organs. Therefore, it is difficult to find the surgical tool in the image acquired by the camera even in a case in which the discriminator is used. On the other hand, it is considered that a discriminator trained to detect a surgical tool from a radiographic image is used to detect the surgical tool from the radiographic image captured after surgery. However, the surgical tool, such as a suture needle, becomes a shadow that is difficult to distinguish from a structure, such as a bone in the subject, or a stent graft or the like inserted into the body in the radiographic image depending on its posture. Therefore, even in a case in which the discriminator is used, there is a possibility that the surgical tool will not be detected with high accuracy.

SUMMARY OF THE INVENTION

The present disclosure has been made in view of the above-mentioned problems, and an object of the present disclosure is to provide a technique that can reliably prevent a surgical tool from remaining in the body of a patient after surgery.

According to an aspect of the present disclosure, there is provided a learning device comprising at least one processor. The processor performs machine learning, which uses a radiographic image that does not include a suture needle as a surgical tool and a surgical tool image that includes the suture needle in a posture different from a linear posture as training data, to construct a trained model for detecting a region of the suture needle from an input radiographic image.

The linear posture means a posture in which the shape of the suture needle on a projected plane is linear in a case in which the suture needle is projected onto the plane.

In addition, the learning device according to the aspect of the present disclosure, the surgical tool image may be acquired by performing radiography on the suture needle in the posture different from the linear posture.

Further, in the learning device according to the aspect of the present disclosure, the surgical tool image may be acquired by a method other than radiography.

Furthermore, in the learning device according to the aspect of the present disclosure, the processor may combine the radiographic image that does not include the surgical tool and the surgical tool image to derive a composite image.

The processor may perform machine learning using the composite image as the training data.

Moreover, in the learning device according to the aspect of the present disclosure, the processor may combine the radiographic image and the surgical tool image with combination parameters corresponding to characteristics of at least one of the radiographic image or the surgical tool to derive the composite image.

Moreover, in the learning device according to the aspect of the present disclosure, the processor may set the combination parameters according to at least one of radiation absorptivity of the surgical tool, a degree of scattering of radiation in the radiographic image, beam hardening in the radiographic image, or noise corresponding to imaging conditions of the radiographic image.

According to another aspect of the present disclosure, there is provided a trained model that is constructed by the learning device according to the present disclosure.

According to still another aspect of the present disclosure, there is provided a radiographic image processing device comprising at least one processor. The processor acquires a plurality of radiographic images of a subject captured in different directions, sequentially detects a region of a suture needle as a surgical tool from the plurality of radiographic images using a trained model constructed by the learning device according to the present disclosure, determines that the surgical tool is included in the subject in a case in which the region of the surgical tool is detected from at least one of the radiographic images, and determines that the surgical tool is not included in the subject in a case in which the region of the surgical tool is not detected from all of the radiographic images.

In addition, according to yet another aspect of the present disclosure, there is provided a learning method comprising: performing machine learning, which uses a radiographic image that does not include a suture needle as a surgical tool and a surgical tool image that includes the suture needle in a posture different from a linear posture as training data, to construct a trained model for detecting a region of the suture needle from an input radiographic image.

In addition, according to still yet another aspect of the present disclosure, there is provided a radiographic image processing method comprising: acquiring a plurality of radiographic images of a subject captured in different directions; sequentially detecting a region of a suture needle as a surgical tool from the plurality of radiographic images using a trained model constructed by the learning device according to the present disclosure; determining that the surgical tool is included in the subject in a case in which the region of the surgical tool is detected from at least one of the radiographic images; and determining that the surgical tool is not included in the subject in a case in which the region of the surgical tool is not detected from all of the radiographic images.

In addition, programs that cause a computer to perform the learning method and the radiographic image processing method according to the present disclosure may be provided.

According to the present disclosure, it is possible to reliably prevent a surgical tool from remaining in the body of a patient after surgery.

DETAILED DESCRIPTION

Figure 1:
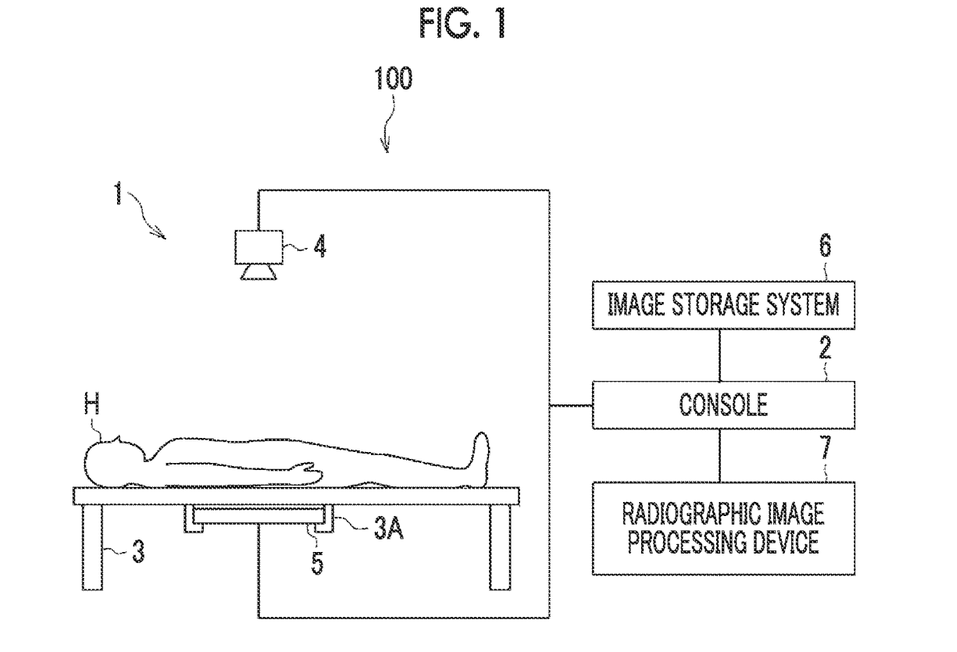
FIG. 1 is a block diagram schematically illustrating a configuration of a radiography system to which a radiographic image processing device according to an embodiment of the present disclosure is applied.

Hereinafter, embodiments of the present disclosure will be described with reference to the drawings. FIG. 1 is a block diagram schematically illustrating the configuration of a radiography system to which a learning device and a radiographic image processing device according to an embodiment of the present disclosure are applied. As illustrated in FIG. 1, a radiography system 100 according to this embodiment acquires a radiographic image of a subject H that is a patient after a surgical operation and detects a surgical tool included in the radiographic image. The radiography system 100 according to this embodiment comprises an imaging apparatus 1, a console 2, an image storage system 6, and a radiographic image processing device 7.

The imaging apparatus 1 detects radiation, which has been emitted from a radiation source 4, such as an X-ray source, and transmitted through a subject H, with a radiation detector 5 to acquire a radiographic image of the subject H that lies supine on an operating table 3. The radiographic image is input to the console 2.

Further, the radiation detector 5 is a portable radiation detector and is attached to the operating table 3 by an attachment portion 3A that is provided in the operating table 3. In addition, the radiation detector 5 may be fixed to the operating table 3.

The console 2 has a function of controlling the imaging apparatus 1 using, for example, an imaging order and various kinds of information acquired from a radiology information system (RIS) (not illustrated) or the like through a network, such as a wireless communication local area network (LAN), and commands or the like directly issued by an engineer or the like. For example, in this embodiment, a server computer is used as the console 2.

The image storage system 6 is a system that stores image data of the radiographic images captured by the imaging apparatus 1. The image storage system 6 extracts an image corresponding to a request from, for example, the console 2 and the radiographic image processing device 7 from the stored radiographic images and transmits the image to a device that is the source of the request. A specific example of the image storage system 6 is a picture archiving and communication system (PACS).

Next, the radiographic image processing device according to this embodiment will be described. In addition, the radiographic image processing device 7 according to this embodiment includes the learning device according to this embodiment. In the following description, it is assumed that the radiographic image processing device represents the device.

Figure 2:
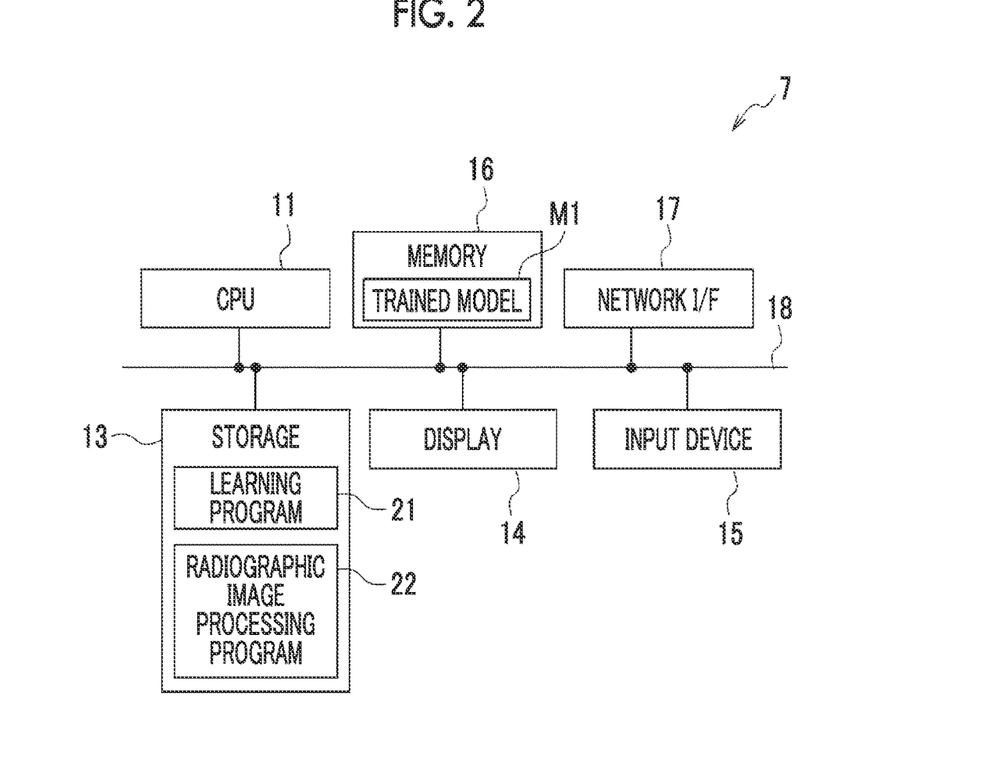
FIG. 2 is a diagram schematically illustrating a configuration of the radiographic image processing device according to this embodiment.

First, the hardware configuration of the radiographic image processing device according to this embodiment will be described with reference to FIG. 2. As illustrated in FIG. 2, the radiographic image processing device 7 is a computer, such as a workstation, a server computer, or a personal computer, and comprises a central processing unit (CPU) 11, a non-volatile storage 13, and a memory 16 as a temporary storage area. In addition, the radiographic image processing device 7 comprises a display 14, such as a liquid crystal display, an input device 15, such as a keyboard and a mouse, and a network interface (I/F) 17 that is connected to a network. The CPU 11, the storage 13, the display 14, the input device 15, the memory 16, and the network I/F 17 are connected to a bus 18. In addition, the CPU 11 is an example of a processor according to the present disclosure.

The storage 13 is implemented by, for example, a hard disk drive (HDD), a solid state drive (SSD), and a flash memory. The storage 13 as a storage medium stores a learning program 21 and a radiographic image processing program 22 which are installed in the radiographic image processing device 7. The CPU 11 reads the learning program 21 and the radiographic image processing program 22 from the storage 13, expands the programs in the memory 16, and executes the expanded learning program 21 and radiographic image processing program 22.

In addition, the learning program 21 and the radiographic image processing program 22 are stored in a storage device of a server computer connected to the network or a network storage so as to be accessed from the outside and are downloaded and installed in the computer forming the radiographic image processing device 7 on demand. Alternatively, the programs are recorded on a recording medium, such as a digital versatile disc (DVD) or a compact disc read only memory (CD-ROM), are distributed and installed in the computer forming the radiographic image processing device 7 from the recording medium.

Figure 3:
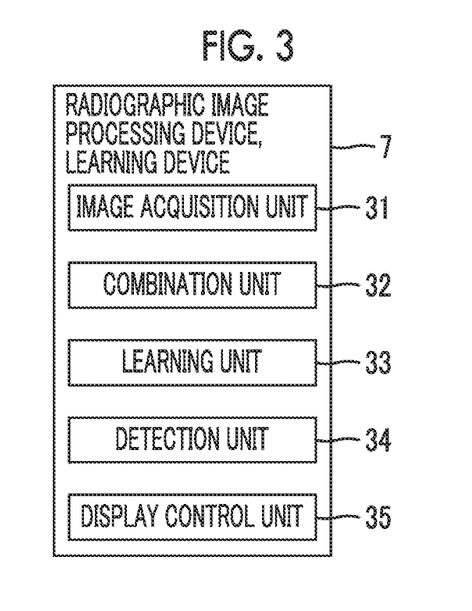
FIG. 3 is a diagram illustrating the functional configuration of the radiographic image processing device according to this embodiment.

Next, the functional configuration of the radiographic image processing device according to this embodiment will be described. FIG. 3 is a diagram illustrating the functional configuration of the radiographic image processing device according to this embodiment. As illustrated in FIG. 3, the radiographic image processing device (learning device) 7 comprises an image acquisition unit 31, a combination unit 32, a learning unit 33, a detection unit 34, and a display control unit 35. Then, the CPU 11 executes the learning program 21 and the radiographic image processing program 22 to function as the image acquisition unit 31, the combination unit 32, the learning unit 33, the detection unit 34, and the display control unit 35.

In addition, the image acquisition unit 31, the combination unit 32, and the learning unit 33 are an example of the learning device according to this embodiment. The image acquisition unit 31, the detection unit 34, and the display control unit 35 are an example of the radiographic image processing device 7 according to this embodiment.

Figure 4:
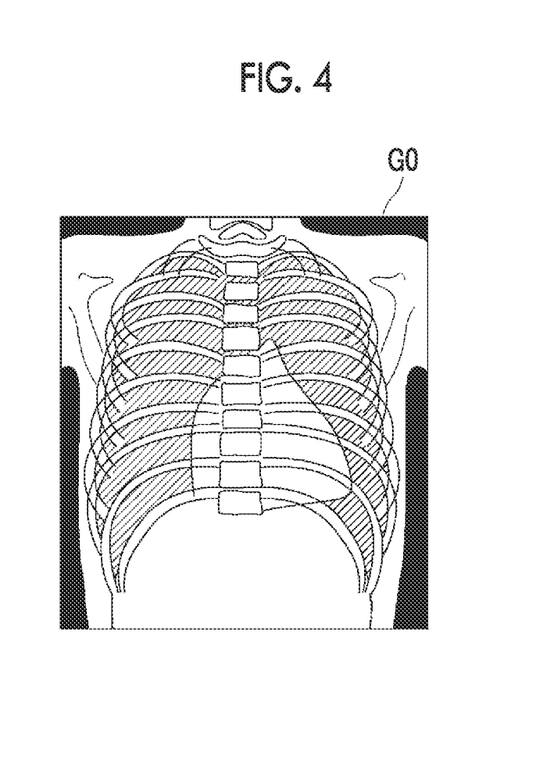
FIG. 4 is a diagram illustrating a radiographic image for generating a composite image.

The image acquisition unit 31 acquires a radiographic image G0 that is used as training data for training a learning model M0, which will be described below, from the image storage system 6 through the network I/F 17. FIG. 4 is a diagram illustrating the radiographic image G0. In addition, FIG. 4 illustrates the radiographic image G0 of the chest of the human body as a target part. However, the target part included in the radiographic image G0 is not limited thereto. As illustrated in FIG. 4, the radiographic image G0 does not include the surgical tool.

Further, the image acquisition unit 31 drives the radiation source 4 to irradiate the subject H after surgery with radiation and detects the radiation transmitted through the subject H using the radiation detector 5 to acquire a target radiographic image to be subjected to a surgical tool detection process. In addition, in this embodiment, a plurality of target radiographic images having different imaging directions are acquired. Specifically, a plurality of target radiographic images having different imaging directions are acquired by changing the position of the radiation source 4 or the orientation of the subject H to capture the images of the subject H in different directions.

Furthermore, the image acquisition unit 31 also acquires a surgical tool image E0 that is used as the training data for training the learning model M0 from the image storage system 6. The surgical tool image E0 may be an image acquired by performing radiography on the surgical tool or may be an image acquired by a method other than radiography. The image acquired by a method other than radiography is an image obtained by two-dimensionally projecting a three-dimensional model indicating the surgical tool created by computer graphics or the like. In addition, in this embodiment, it is assumed that a suture needle for sewing up a wound or an incision is used as the surgical tool.

Figure 5:
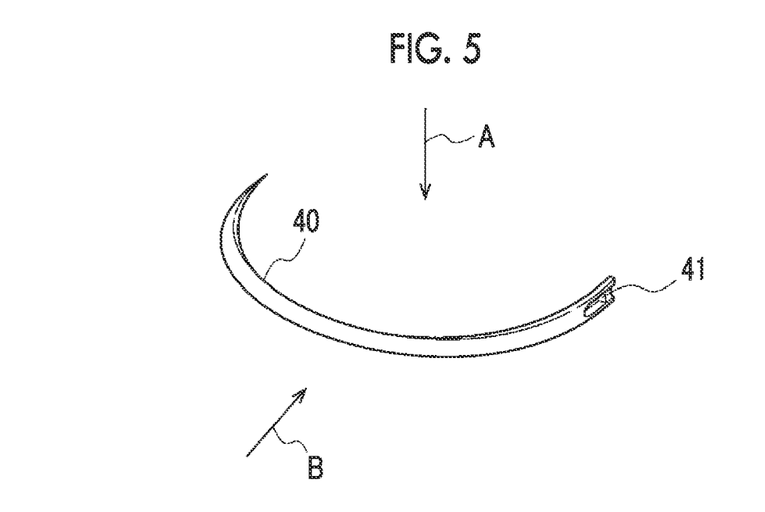
FIG. 5 is a diagram illustrating a suture needle.
Figure 6:
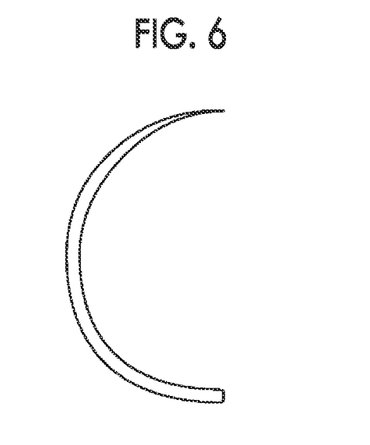
FIG. 6 is a diagram illustrating the suture needle as viewed from the direction of an arrow A illustrated in FIG. 5.
Figure 7:
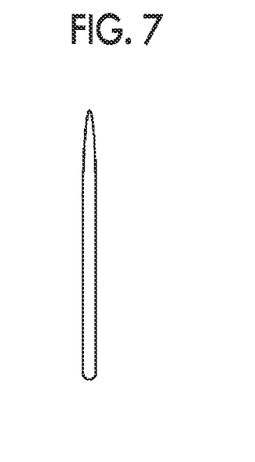
FIG. 7 is a diagram illustrating the suture needle as viewed from the direction of an arrow B illustrated in FIG. 5.

FIG. 5 is a diagram illustrating a suture needle. As illustrated in FIG. 5, a suture needle 40 is curved, and a hole 41 through which a suture thread is passed is formed in a rear end portion. In addition, the maximum width is about several millimeters to several centimeters. Here, FIG. 6 illustrates the suture needle as viewed from the direction of an arrow A illustrated in FIG. 5, and FIG. 7 illustrates the suture needle as viewed from the direction of an arrow B. The direction of the arrow A is a direction orthogonal to the plane on which the suture needle 40 is placed. The direction of the arrow B is a direction in which the plane on which the suture needle 40 is placed extends.

In a case in which the suture needle 40 is viewed from the direction of the arrow A, it is possible to recognize the suture needle 40 at first glance from the shape as illustrated in FIG. 6.

On the other hand, in a case in which the suture needle 40 is viewed from the direction of the arrow B, it is difficult to recognize the suture needle 40 at first glance since the suture needle 40 has a linear shape as illustrated in FIG. 7. In particular, in a case in which the suture needle 40 remains in the body of the subject H and the direction in which the suture needle 40 is irradiated with radiation is aligned with the direction of the arrow B illustrated in FIG. 5, the suture needle 40 is a high-brightness shadow having a linear shape with a length of about several millimeters to several centimeters in the radiographic image. The shadow of the suture needle 40 is indistinguishable from the bone of the subject H or an artificial object, such as a stent graft, inserted into the body of the subject H. Therefore, in a case in which the suture needle included in the surgical tool image E0 has a linear shape as illustrated in FIG. 7, the use of the surgical tool image E0 makes it possible to train the learning model M0 so as to detect the suture needle 40 with high accuracy.

Figure 8:
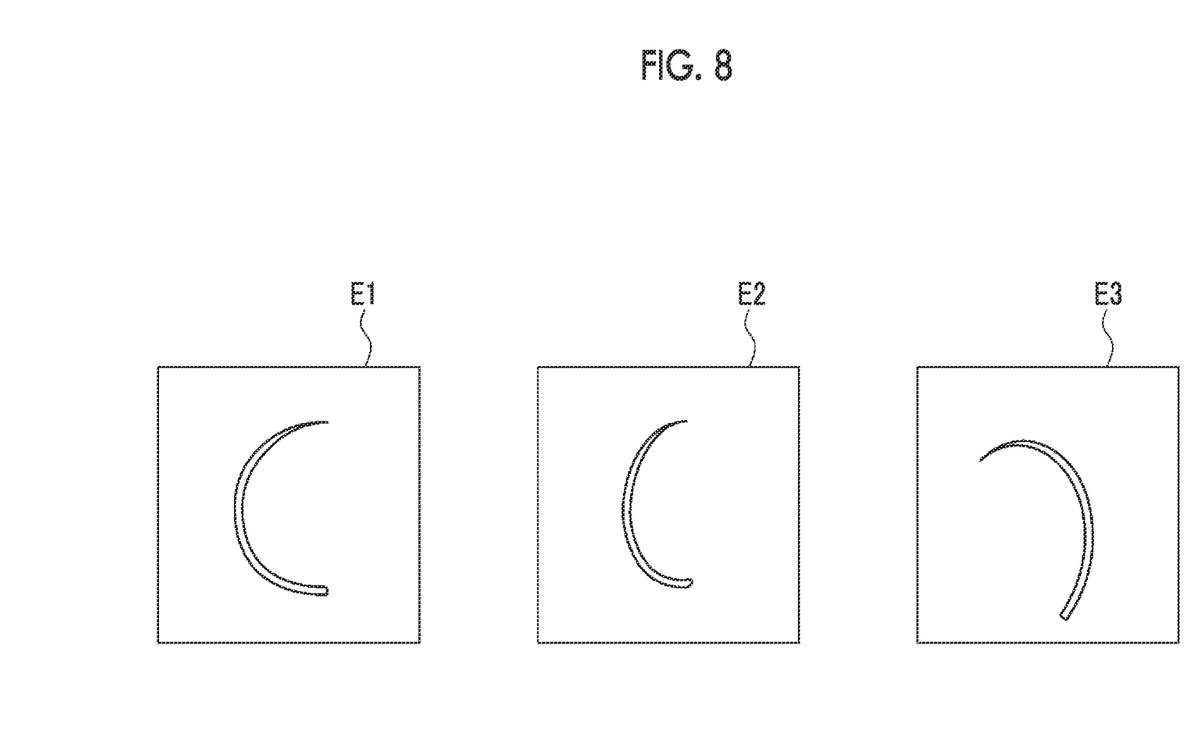
FIG. 8 is a diagram illustrating a surgical tool image.

Therefore, in this embodiment, the surgical tool image E0 including the suture needle 40 in a posture different from the linear posture is used. FIG. 8 is a diagram illustrating the surgical tool images. FIG. 8 illustrates three surgical tool images. As illustrated in FIG. 8, the postures of the suture needle 40 included in three surgical tool images µl to E3 are different from the linear posture.

Figure 9:
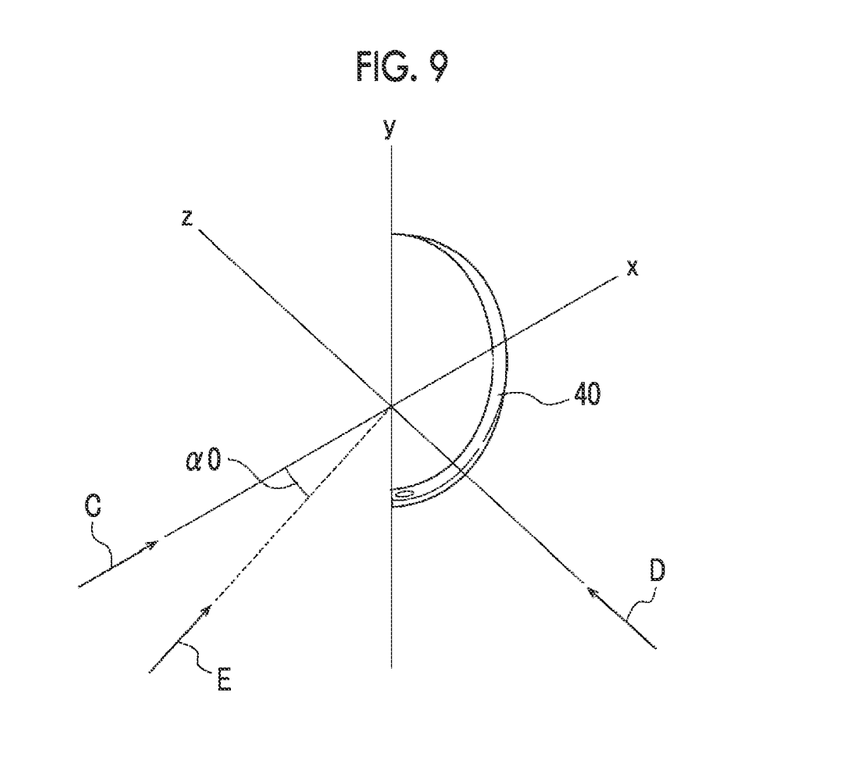
FIG. 9 is a diagram illustrating the posture of the suture needle.

In addition, the linear posture may be a substantially linear posture having an allowable error. For example, as illustrated in FIG. 9, the xyz coordinate system is determined for the suture needle 40. In FIG. 9, the xy plane is a plane including an axis connecting both ends of the suture needle 40 along the curved shape of the suture needle 40. In FIG. 9, in a case in which the direction of an arrow C is a line-of-sight direction, the suture needle 40 appears to be linear. On the other hand, in a case in which the direction of an arrow D is the line-of-sight direction, the suture needle 40 appears to be placed on the plane. In a case in which this coordinate system is determined, the posture of the suture needle viewed from a direction (for example, the direction of an arrow E) obtained by rotating the line-of-sight direction by a certain angle α0 around the y-axis from the direction of the arrow C may also be included in the linear posture. In this case, the angle α0 can be, for example, ±5 degrees, but is not limited thereto. Therefore, for the posture of the suture needle 40 included in the surgical tool image E0, the suture needle 40 is viewed from an angle that is equal to or greater than the angle α0 from the direction of the arrow C illustrated in FIG. 9. In addition, the angle α0 illustrated in FIG. 9 is an example and is different from the actual angle.

In a case in which the surgical tool image E0 is a radiographic image, the suture needle 40 may be disposed in the posture in which the irradiation direction of radiation is not aligned with the direction of the arrow C illustrated in FIG. 9, and the radiographic image of the suture needle 40 may be captured. Further, in a case in which the surgical tool image E0 is created by computer graphics or the like, the suture needle may be included in the surgical tool image E0 so as not to have a linear posture. In addition, the surgical tool image E0 may be a photographic image of the surgical tool. In the case of the photographic image, the suture needle may be disposed in the posture in which the direction of the optical axis of a camera is not aligned with the direction of the arrow C illustrated in FIG. 9, and the photographic image of the suture needle 40 may be captured.

In addition, the combination unit 32 combines the surgical tool image E0 with the radiographic image G0 to generate a composite image C0. The combination unit 32 combines the radiographic image G0 and the surgical tool image E0 with combination parameters corresponding to the characteristics of at least one of the radiographic image G0 or the suture needle which is the surgical tool to generate the composite image C0. The combination unit 32 sets the combination parameters according to at least one of the radiation absorptivity of the suture needle which is the surgical tool, the degree of scattering of radiation by the surgical tool, beam hardening in the radiographic image G0, or noise corresponding to the imaging conditions of the radiographic image G0.

In addition, the radiographic image G0 may be displayed on the display 14, and the position of the surgical tool image E0 and the orientation of the surgical tool image E0 in the radiographic image G0 may be designated by an instruction input by the operator through the input device 15.

Figure 10:
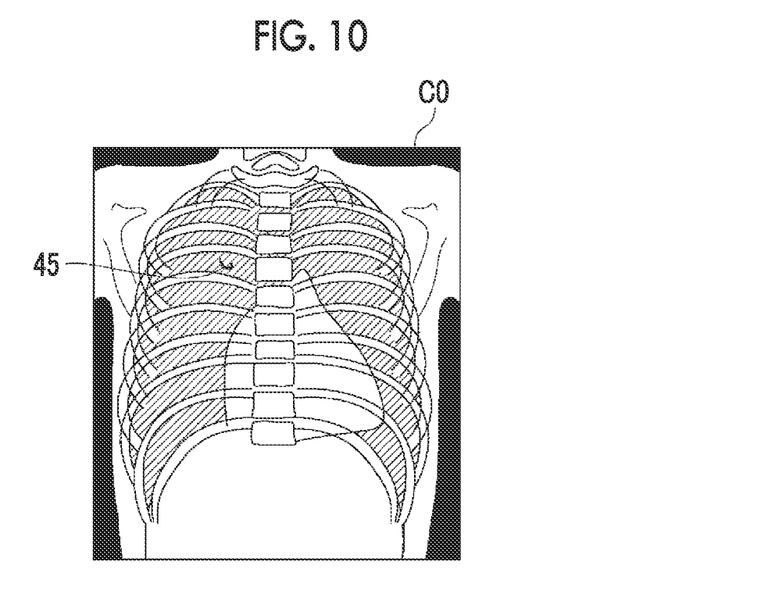
FIG. 10 is a diagram illustrating a composite image.

In this embodiment, for example, it is assumed that the combination unit 32 generates the composite image C0 using the following Expression (1). That is, for the pixels (x, y) of a region of the radiographic image G0 which is combined with the surgical tool image E0, the combination unit 32 subtracts a pixel value E0(x, y) of the surgical tool image E0 weighted by a weight coefficient w1 from a pixel value G0(x, y) of the radiographic image G0 to derive a pixel value C0(x, y) of the composite image C0. In addition, the weight coefficient w1 has a value that is equal to or greater than 0 and equal to or less than 1. The weight coefficient w1 is included in the combination parameters according to this embodiment. FIG. 10 is a diagram illustrating a composite image. As illustrated in FIG. 10, in the composite image C0, a shadow 45 of the suture needle is included in the right lung of the subject.

$$C0(x,y)=G0(x,y)-w1\cdot E0(x,y) \tag{1}$$

Here, in a case in which the radiation absorptivity of the surgical tool is high, the contrast of the surgical tool is high in a radiographic image acquired by performing radiography for the surgical tool. For example, in a case in which the surgical tool is a metal tool, such as a suture needle, scissors, or a scalpel, the contrast of the radiographic image of the surgical tool is high. Therefore, in a case in which weighted subtraction between the radiographic image G0 and the surgical tool image E0 is performed, the combination unit 32 increases the weight coefficient w1 for the surgical tool image E0 such that the contrast of the surgical tool is not too high in the composite image C0.

Further, the contrast of the radiographic image G0 is reduced due to the scattering of radiation. The influence of the scattering of radiation becomes larger as the body thickness of the subject H becomes larger. In addition, as the body thickness of the subject H becomes larger, the density of a subject region included in the radiographic image G0 becomes lower. Therefore, the combination unit 32 derives the average value of the density of the subject region included in the radiographic image G0, reduces the weight coefficient w1 such that a density difference between the radiographic image G0 and the surgical tool image E0 becomes smaller as the average value become smaller, that is, the body thickness of the subject H becomes larger, and generates the composite image C0.

Here, beam hardening occurs in which, as the tube voltage applied to the radiation source 4 becomes higher and the energy of radiation becomes higher, a lower-energy component of the radiation is absorbed by the subject H and the energy of the radiation becomes higher while the radiation is transmitted through the subject H. In a case in which the beam hardening occurs, the contrast of the radiographic image decreases. Further, the increase in the energy of radiation due to the beam hardening becomes more significant as the body thickness of the subject H becomes larger. In addition, as the body thickness of the subject H becomes larger, the density of a subject region included in the radiographic image G0 becomes lower. Therefore, the combination unit 32 derives the average value of the density of the subject region included in the radiographic image G0, reduces the weight coefficient w1 such that a density difference between the radiographic image G0 and the surgical tool image E0 becomes smaller as the average value become smaller, that is, the body thickness of the subject H becomes larger, and generates the composite image C0.

In addition, in a case in which the radiation dose in the imaging conditions is reduced, the amount of noise included in the radiographic image G0 increases. Therefore, in a case in which the radiation dose is small, the combination unit 32 adds noise N(x, y) corresponding to the radiation dose to Expression (1) to generate the composite image C0, as illustrated in the following Expression (2). In this case, the weight coefficient w1 may be a predetermined value or may be set according to at least one of the radiation absorptivity of the surgical tool, the degree of scattering of radiation, or the beam hardening. Further, the noise N(x, y) may be derived in advance according to the radiation dose and stored in the storage 13. In addition, the noise N(x, y) is included in the combination parameters.

$$C0(x,y)=G0(x,y)-w1\cdot E0(x,y)+N(x,y) \tag{2}$$

In this embodiment, the combination unit 32 may change the combination position of the surgical tool image E0 in the radiographic image G0 or the combination parameters to generate a plurality of composite images C0. Therefore, the composite image C0 obtained by combining the surgical tool image E0 with the radiographic image G0 as if the surgical tool image E0 is acquired by radiography is generated. In addition, the composite image C0 may be generated using a plurality of radiographic images G0 having different subjects H.

Further, even in a case in which the surgical tool image E0 is acquired by performing radiography on the surgical tool, the composite image C0 may be generated by combining the surgical tool image E0 with the radiographic image G0 while appropriately setting the combination parameters.

A plurality of composite images C0 are generated and stored in the image storage system 6. Alternatively, the composite images C0 are stored in the storage 13 of the radiographic image processing device 7. In addition to the composite images C0, a plurality of radiographic images G0 are also stored in the storage 13.

The learning unit 33 trains the learning model M0 using training data consisting of the radiographic image G0 that does not include the surgical tool and training data including the composite image C0 and the correct answer data specifying the region of the surgical tool in the composite image C0. In addition, the learning unit 33 trains the learning model M0 using a plurality of training data items. The correct answer data is the coordinates of the upper left corner and the coordinates of the lower right corner of a region surrounding the suture needle in the composite image C0, or the coordinates of the lower left corner and the coordinates of the upper right corner of the region. In addition, the correct answer data may be generated by a manual operation while viewing the composite image C0.

A machine learning model can be used as the learning model M0. One example of the machine learning model is a neural network model. Examples of the neural network model include a simple perceptron, a multilayer perceptron, a deep neural network, a convolutional neural network, a deep belief network, a recurrent neural network, and a stochastic neural network. In this embodiment, it is assumed that the convolutional neural network is used as the learning model M0.

In a case in which an image is input, the learning model M0 is trained so as to output the probability that each pixel of the image will be the region of the surgical tool. The probability is a value that is equal to or greater than 0 and equal to or less than 1. A region consisting of the pixels having the probability which has been output from the learning model M0 and is equal to or greater than a predetermined threshold value is the region of the surgical tool. The learning unit 33 inputs the training data to the learning model M0 and directs the learning model M0 to output the probability of each pixel being the region of the surgical tool. Then, the difference between the region consisting of the pixels having the probability which has been output from the learning model M0 and is equal to or greater than the predetermined threshold value and the region indicated by the correct answer data included in the training data is derived as a loss.

Here, in a case in which the radiographic image G0 is input as the training data to the learning model M0, the radiographic image G0 does not include the surgical tool. Therefore, the probability of each pixel being the region of the surgical tool has to be zero. However, the learning model M0 that has not been completely trained outputs a value greater than 0 as the probability of each pixel being the region of the surgical tool. Therefore, in a case in which the radiographic image G0 is input as the training data, the difference between the probability output for each pixel and 0 is a loss.

On the other hand, in a case in which the composite image C0 is input as the training data to the learning model M0, the surgical tool is included in the composite image C0. Therefore, the probability that the pixels in the region defined by the correct answer data in the composite image C0 will be the region of the surgical tool has to be 1. However, the learning model M0 that has not been completely trained outputs a value less than 1 as the probability of each pixel being the region of the surgical tool. Therefore, in a case in which the surgical tool image E0 is input as the training data, the difference between the probability output for each pixel and 1 is a loss.

The learning unit 33 trains the learning model M0 on the basis of the loss. Specifically, for example, a kernel coefficient in the convolutional neural network and a weight for the connection of neural networks are derived so as to reduce the loss. The learning unit 33 repeats learning until the loss is equal to or less than a predetermined threshold value. Therefore, a trained model M1 is constructed such that, in a case in which the radiographic image G0 is input, the probability that the entire image will be the region of the surgical tool approaches zero. Further, the trained model M1 is constructed such that, in a case in which the composite image C0 is input, the probability that the region defined by the correct answer data will be the region of the surgical tool approaches 1. The constructed trained model M1 is stored in the memory 16.

In a case in which a radiographic image including the surgical tool is input to the trained model M1 constructed in this way, the trained model M1 outputs a probability close to 1 for the pixels in the region of the surgical tool in the radiographic image and outputs a probability close to 0 for the pixels in the other regions.

Figure 11:
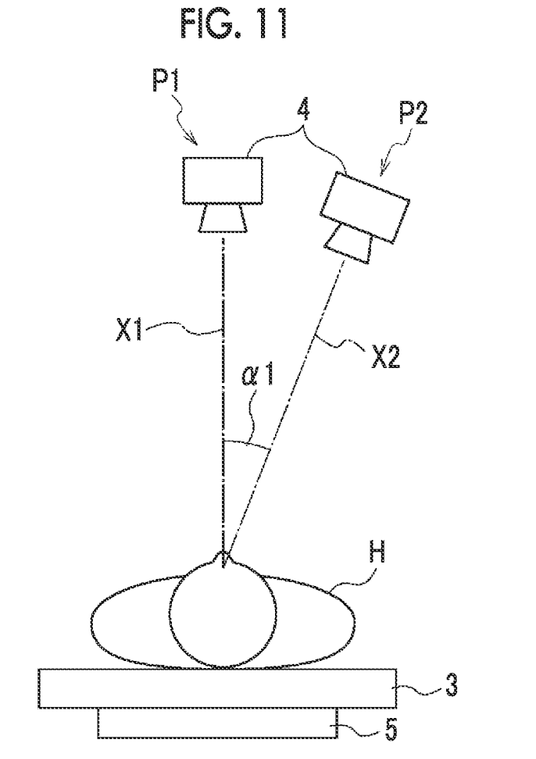
FIG. 11 is a diagram illustrating the capture of a plurality of target radiographic images.

The detection unit 34 detects the region of the surgical tool from a plurality of target radiographic images Ti (i=1 to n, n is the number of target radiographic images) obtained by capturing the images of the subject H after surgery in different directions, using the trained model M1. FIG. 11 is a diagram illustrating the capture of a plurality of target radiographic images. As illustrated in FIG. 11, in this embodiment, for example, it is assumed that the radiation source 4 is moved to two positions of a first position P1 and a second position P2 and two target radiographic images are acquired. An optical axis X1 of the radiation emitted from the radiation source 4 at the first position P1 is orthogonal to the radiation detector 5. An optical axis X2 of the radiation emitted from the radiation source 4 at the second position P2 forms an angle $\alpha 1$ with respect to the optical axis X1. Here, in this embodiment, in the surgical tool image E0 used as the training data for training the learning model M0, the suture needle 40 is viewed from an angle that is equal to or greater than the angle $\alpha 0$ from the direction of the arrow C illustrated in FIG. 9. Therefore, in a case in which the plurality of target radiographic images Ti are acquired, it is preferable that the angle $\alpha 1$ formed between the optical axis X1 and the optical axis X2 is equal to or greater than the angle $\alpha 0$ illustrated in FIG. 9.

In this embodiment, the trained model M1 has been trained using the composite image C0 in which the suture needle is included in a linear posture. In a case in which the suture needle is included in the subject H, the suture needle included in the target radiographic images Ti may be linear depending on the posture of the suture needle with respect to the direction in which radiation is incident on the subject H. However, in a case in which there are a plurality of imaging directions, even though the suture needle is linear in one target radiographic image, the suture needle is not linear in the other target radiographic images.

Therefore, the detection unit 34 sequentially selects the plurality of target radiographic images Ti and detects, as the region of the surgical tool, a region consisting of the pixels, for which the probability output from the trained model M1 is equal to or greater than a predetermined threshold value Th1, for each pixel of the selected target radiographic image. In addition, for all of the pixels of the selected target radiographic image Ti, in a case in which the probability output from the trained model M1 is less than the threshold value Th1, the detection unit 34 outputs a detection result indicating that the selected target radiographic image Ti does not include the surgical tool. Further, in a case in which the detection result indicating that the surgical tool is not included in all of the target radiographic images Ti is obtained, the detection unit 34 outputs the detection result indicating that the surgical tool does not remain in the subject H.

Figure 12:
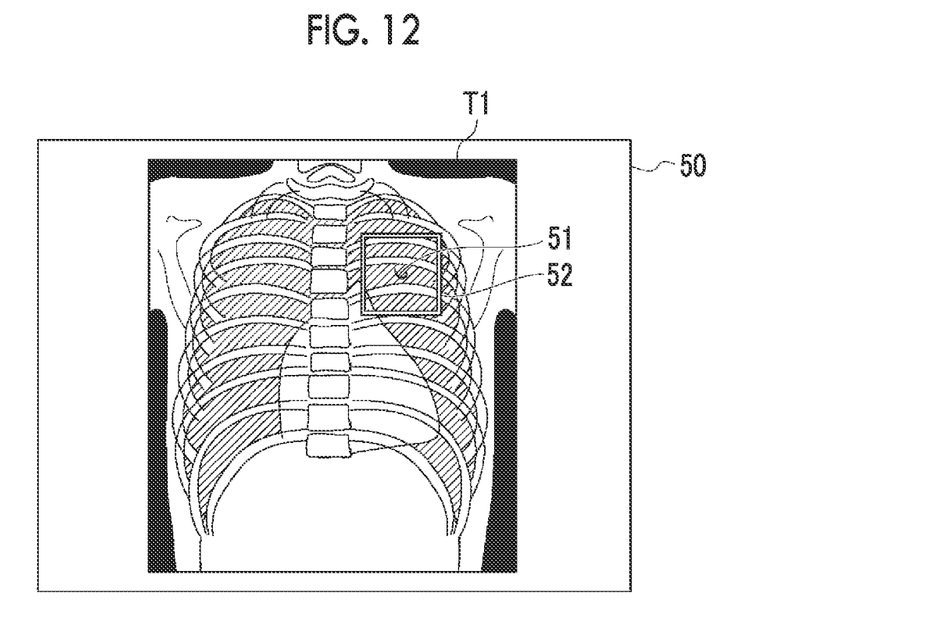
FIG. 12 is a diagram illustrating a radiographic image display screen in a case in which a surgical tool is detected.

In a case in which the region of the surgical tool is detected from any of the target radiographic images Ti, the display control unit 35 displays the target radiographic image (for example, T1), in which the region of the surgical tool has been detected, on the display 14 such that the region of the surgical tool is highlighted. FIG. 12 is a diagram illustrating a radiographic image display screen. As illustrated in FIG. 12, the target radiographic image Ti is displayed on a display screen 50, and a region 51 of the suture needle as the surgical tool included in the target radiographic image Ti is surrounded with a rectangular region 52 such that the region 51 of the surgical tool is highlighted. In addition, the rectangular region 52 is illustrated in white in FIG. 12. However, the rectangular region 52 may be colored. Further, instead of giving the rectangular region 52, a mark, such as an arrow or an asterisk, may be given in the vicinity of the region of the surgical tool to highlight the region of the surgical tool. Further, the region 51 of the surgical tool may be masked to be highlighted. In addition, the mask may be colored.

In addition, in a case in which the target radiographic image T1 in which the region of the surgical tool has been highlighted is displayed, image processing for display, such as a gradation conversion process or a density conversion process, may be performed on the target radiographic image T1 in order to easily observe the target radiographic image T1. The display control unit 35 may perform the image processing for display, or an image processing unit for performing the image processing for display may be separately provided.

Figure 13:
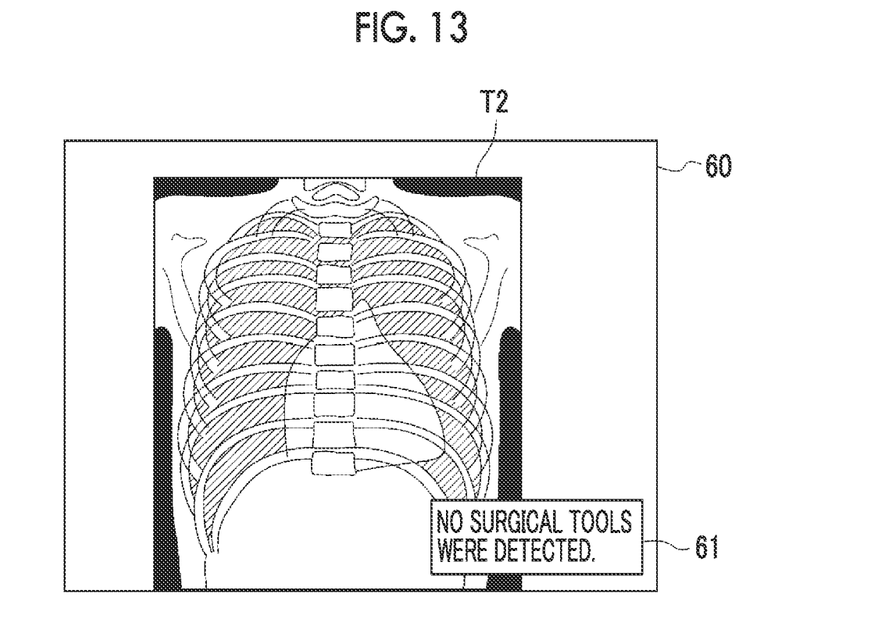
FIG. 13 is a diagram illustrating a notification screen in a case in which a region of the surgical tool is not detected.

In addition, in a case in which the detection unit 34 does not detect the region of the surgical tool from all of the target radiographic images Ti, the display control unit 35 notifies the fact. FIG. 13 is a diagram illustrating a target radiographic image display screen in a case in which the surgical tool is not detected. As illustrated in FIG. 13, a notification 61 of "No surgical tools were detected." is displayed on a display screen 60 so as to be superimposed on any one (for example, T2) of the plurality of target radiographic images Ti. In addition, instead of the notification 61, for example, an icon or a mark indicating that no surgical tools were detected may be displayed. Further, the turn-on and turn-off of the display of the notification 61 may be switched by an instruction from the input device 15.

Figure 14:
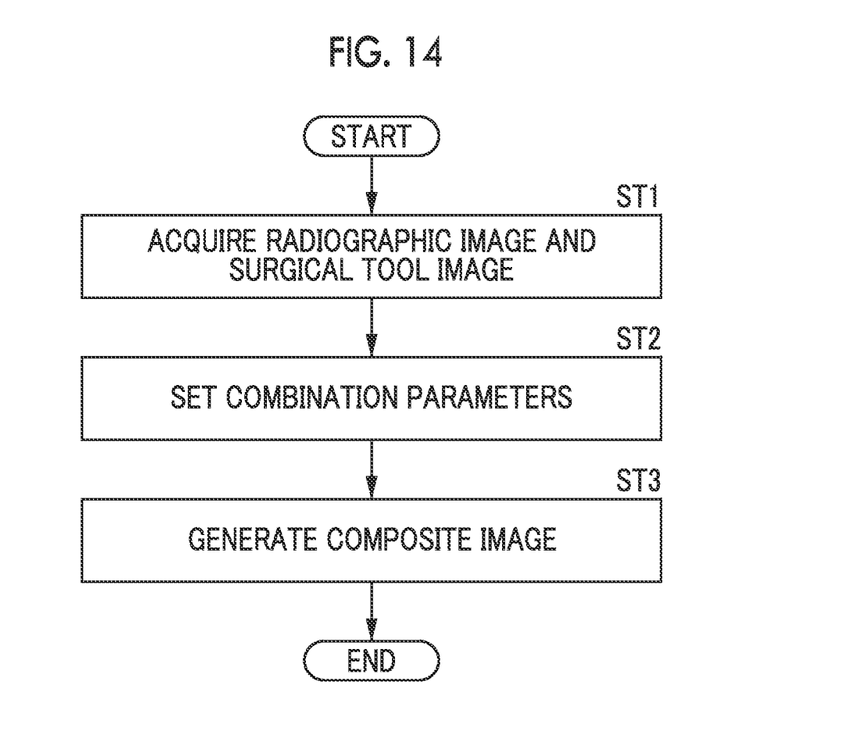
FIG. 14 is a flowchart illustrating a composite image generation process performed in this embodiment.

Next, a process performed in this embodiment will be described. FIG. 14 is a flowchart illustrating a process of generating the composite image used for learning in this embodiment. First, the image acquisition unit 31 acquires the radiographic image G0 and the surgical tool image E0 (Step ST1). Then, the combination unit 32 sets combination parameters for the radiographic image G0 and the surgical tool image E0 (Step ST2) and combines the radiographic image G0 and the surgical tool image E0 according to the combination parameters to generate the composite image C0 (Step ST3). Then, the process ends.

Figure 15:
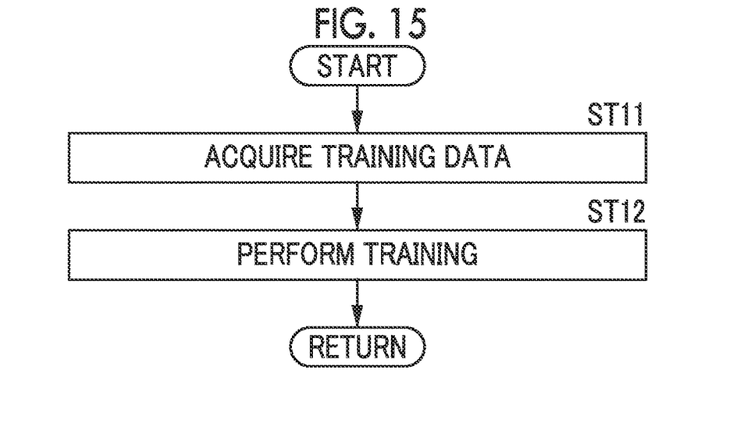
FIG. 15 is a flowchart illustrating a learning process performed in this embodiment.

Next, a learning process according to this embodiment will be described. FIG. 15 is a flowchart illustrating the learning process performed in this embodiment. The learning unit 33 acquires training data consisting of the composite image C0 and correct answer data, and training data consisting of the radiographic image G0 without including the surgical tool (Step ST11), inputs the training data to the learning model M0, acquires the extraction result of the region of the surgical tool, trains the learning model M0 using the loss based on the difference from the correct answer data (Step ST12), and returns to Step ST11. Then, the learning unit 33 repeats the process in Steps ST11 and ST12 until the loss reaches a predetermined threshold value and ends the training. In addition, the learning unit 33 may repeat the training a predetermined number of times and end the training. Therefore, the learning unit 33 constructs the trained model M1.

Figure 16:
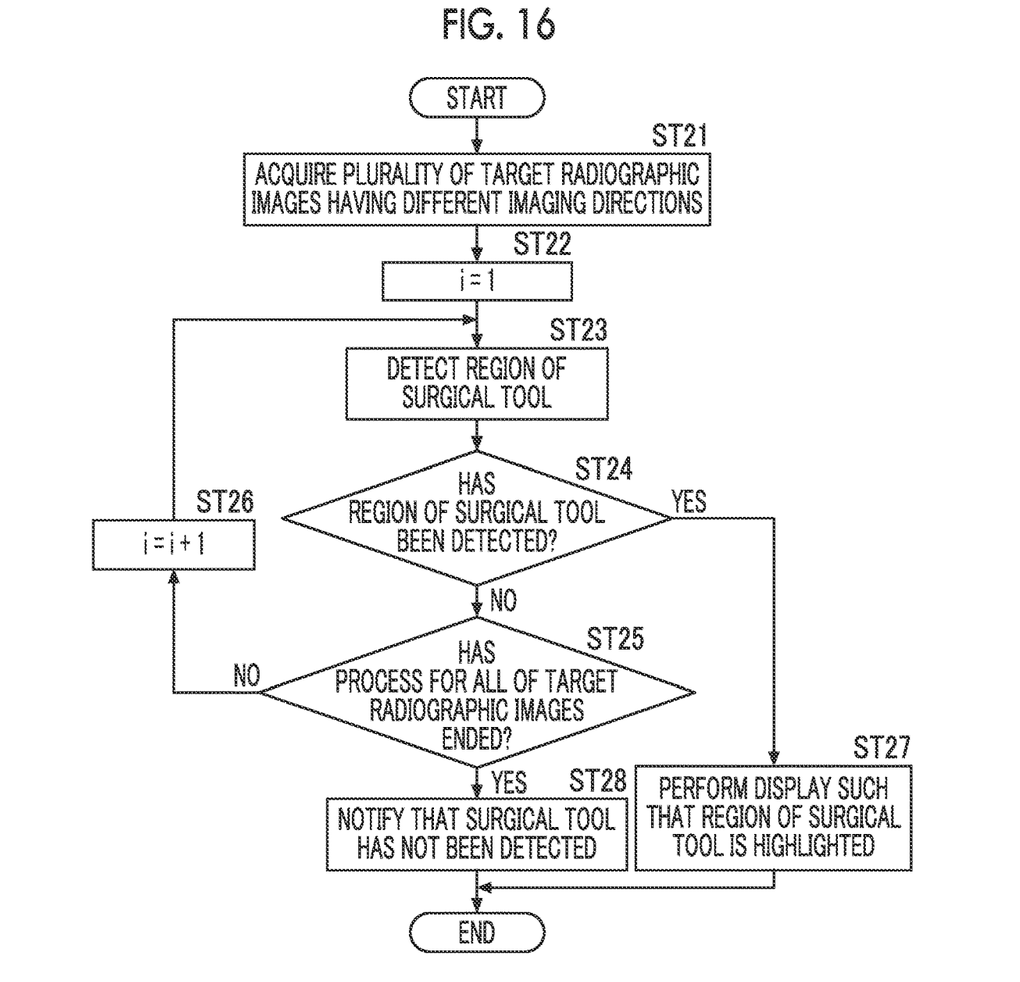
FIG. 16 is a flowchart illustrating a detection process performed in this embodiment.

Next, a surgical tool region detection process according to this embodiment will be described. FIG. 16 is a flowchart illustrating the detection process performed in this embodiment. The image acquisition unit 31 acquires a plurality of target radiographic images Ti which are detection targets and have different imaging directions (Step ST21). The detection unit 34 sets the target radiographic image Ti which is the detection target as a first radiographic image (i=1; Step ST22) and detects the region of the surgical tool from the target radiographic image Ti using the trained model M1 (Step ST23). In a case in which the region of the surgical tool is not detected from the target radiographic image (Step ST24: NO), the detection unit 34 determines whether or not the detection process has ended for all of the target radiographic images Ti (Step ST25). In a case in which the determination result in Step ST25 is "No", the detection unit 34 changes the detection target to the next target radiographic image (i=i+1; Step ST26) and returns to Step ST23.

In a case in which the region of the surgical tool is detected from the target radiographic image (Step ST24: YES), the display control unit 35 displays the target radiographic image in which the region of the surgical tool has been highlighted on the display 14 (Step ST27). Then, the process ends. On the other hand, in a case in which the determination result in Step ST25 is "Yes", the display control unit 35 notifies that the region of the surgical tool has not been detected (Step ST28). Then, the process ends.

Here, since the surgical tool, such as the suture needle, is a linear shadow in the radiographic image depending on its posture, it is difficult to distinguish the surgical tool from a structure, such as a bone in the subject, or a stent graft or the like inserted into the body. Therefore, even in a case in which the trained model M1 that has been trained to detect the suture needle is used, there is a possibility that the surgical tool will not be detected with high accuracy.

In this embodiment, machine learning, which uses, as training data, a radiographic image that does not include the surgical tool and a surgical tool image that includes a suture needle in a posture different from a linear posture in a case in which the suture needle is included in a radiographic image, is performed to construct the trained model M1 that detects the region of the suture needle as the surgical tool from the target radiographic image. Further, in this embodiment, a plurality of target radiographic images Ti having different imaging directions are acquired, and the trained model M1 is used to detect the region of the surgical tool from the plurality of target radiographic images Ti.

In a case in which the suture needle is included in the subject H, the suture needle included in the target radiographic images Ti may be linear depending on the posture of the suture needle with respect to the irradiation direction of radiation. However, in a case in which there are a plurality of imaging directions, even though the suture needle is linear in one target radiographic image, the suture needle is not linear in the other target radiographic images.

Therefore, according to this embodiment, it is possible to detect the region of the surgical tool from the target radiographic image regardless of the posture of the suture needle, which is the surgical tool, in the subject. As a result, it is possible to reliably prevent the surgical tool from remaining in the body of a patient after surgery.

In addition, since the radiographic image which includes the surgical tool and is necessary for training the learning model M0 is extremely rare, it is difficult to collect a large number of radiographic images in order to train the learning model M0. In this embodiment, the learning model M0 is trained using the radiographic image G0 and the surgical tool image E0 as the training data. Therefore, it is possible to prepare a sufficient amount of training data. As a result, it is possible to construct the trained model M1 detecting the surgical tool with high accuracy.

Further, the radiographic image G0 and the surgical tool image E0 are combined using the combination parameters to generate the composite image C0. Therefore, it is possible to generate the composite image C0 obtained by combining the surgical tool image E0 with the radiographic image G0 as if the surgical tool image E0 is acquired together with the subject by radiography.

In addition, in the above-described embodiment, the trained model M1 is constructed by using the composite image C0 obtained by combining the radiographic image G0 and the surgical tool image E0 as the training data. However, the present disclosure is not limited thereto. The trained model M1 may be constructed by independently using each of the radiographic image G0 and the surgical tool image E0 as the training data. In a case in which the surgical tool image E0 is used as the training data, the coordinates surrounding the region of the surgical tool in the surgical tool image E0 are used as the correct answer data. Further, in this case, the trained model M1 is constructed such that, in a case in which the surgical tool image E0 is input, the probability that the region defined by the correct answer data will be the region of the surgical tool approaches 1. As such, even in a case in which each of the radiographic image G0 and the surgical tool image E0 is independently used as the training data, similarly to the case in which the composite image C0 is used, it is possible to construct the trained model M1 such that, in a case in which a radiographic image including the surgical tool is input, it outputs the probability close to 1 for the pixels in the region of the surgical tool in the radiographic image and outputs the probability close to 0 for the pixels in the other regions.

In addition, in the above-described embodiment, the radiation is not particularly limited. For example, $\alpha$-rays or $\gamma$-rays other than X-rays can be applied.

In the above-described embodiment, for example, the following various processors can be used as a hardware structure of processing units performing various processes, such as the image acquisition unit 31, the combination unit 32, the learning unit 33, the detection unit 34, and the display control unit 35. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. A learning device comprising:
   at least one processor,
   wherein the processor performs machine learning, which uses a radiographic image that does not include a suture needle as a surgical tool and a surgical tool image that includes the suture needle in a posture different from a linear posture as training data, to construct a trained model for detecting a region of the suture needle from an input radiographic image, and
   wherein the processor combines the radiographic image that does not include the surgical tool and the surgical tool image to derive a composite image and performs machine learning using the composite image as the training data.

2. The learning device according to claim 1,
   wherein the surgical tool image is acquired by performing radiography on the suture needle in the posture different from the linear posture.

3. The learning device according to claim 1,
   wherein the surgical tool image is acquired by a method other than radiography.

4. The learning device according to claim 1,
   wherein the processor combines the radiographic image and the surgical tool image with combination parameters corresponding to characteristics of at least one of the radiographic image or the surgical tool to derive the composite image.

5. The learning device according to claim 4,
   wherein the processor sets the combination parameters according to at least one of radiation absorptivity of the surgical tool, a degree of scattering of radiation in the radiographic image, beam hardening in the radiographic image, or noise corresponding to imaging conditions of the radiographic image.

6. A trained model that is constructed by the learning device according to claim 1.

7. A radiographic image processing device comprising:
   at least one processor,
   wherein the processor acquires a plurality of radiographic images of a subject captured in different directions, sequentially detects a region of a suture needle as a surgical tool from the plurality of radiographic images using a trained model constructed by a learning device, determines that the surgical tool is included in the subject in a case in which the region of the surgical tool is detected from at least one of the radiographic images, and determines that the surgical tool is not included in the subject in a case in which the region of the surgical tool is not detected from all of the radiographic images, and
   wherein the learning device performs machine learning, which uses a radiographic image that does not include a suture needle as a surgical tool and a surgical tool image that includes the suture needle in a posture different from a linear posture as training data, to construct a trained model for detecting a region of the suture needle from an input radiographic image.

8. A learning method comprising:
performing machine learning, which uses a radiographic image that does not include a suture needle as a surgical tool and a surgical tool image that includes the suture needle in a posture different from a linear posture as training data, to construct a trained model for detecting a region of the suture needle from an input radiographic image, and
wherein the method further comprises combining the radiographic image that does not include the surgical tool and the surgical tool image to derive a composite image, and performing machine learning using the composite image as the training data.

9. A radiographic image processing method comprising:
acquiring a plurality of radiographic images of a subject captured in different directions;
sequentially detecting a region of a suture needle as a surgical tool from the plurality of radiographic images using a trained model constructed by a learning device;
determining that the surgical tool is included in the subject in a case in which the region of the surgical tool is detected from at least one of the radiographic images; and
determining that the surgical tool is not included in the subject in a case in which the region of the surgical tool is not detected from all of the radiographic images, and
wherein the learning device performs machine learning, which uses a radiographic image that does not include a suture needle as a surgical tool and a surgical tool image that includes the suture needle in a posture different from a linear posture as training data, to construct a trained model for detecting a region of the suture needle from an input radiographic image.

10. A non-transitory computer-readable storage medium that stores a learning program that causes a computer to perform:
a procedure of performing machine learning, which uses a radiographic image that does not include a suture needle as a surgical tool and a surgical tool image that includes the suture needle in a posture different from a linear posture as training data, to construct a trained model for detecting a region of the suture needle from an input radiographic image, and
wherein the program further causes the computer to perform a procedure of combining the radiographic image that does not include the surgical tool and the surgical tool image to derive a composite image, and a procedure of performing machine learning using the composite image as the training data.

11. A non-transitory computer-readable storage medium that stores a radiographic image processing program that causes a computer to perform:
a procedure of acquiring a plurality of radiographic images of a subject captured in different directions;
a procedure of sequentially detecting a region of a suture needle as a surgical tool from the plurality of radiographic images using a trained model constructed by a learning device;
a procedure of determining that the surgical tool is included in the subject in a case in which the region of the surgical tool is detected from at least one of the radiographic images; and
a procedure of determining that the surgical tool is not included in the subject in a case in which the region of the surgical tool is not detected from all of the radiographic images, and
wherein the learning device performs machine learning, which uses a radiographic image that does not include a suture needle as a surgical tool and a surgical tool image that includes the suture needle in a posture different from a linear posture as training data, to construct a trained model for detecting a region of the suture needle from an input radiographic image.

* * * * *